(12) United States Patent
Tzeng et al.

(10) Patent No.: US 8,304,225 B2
(45) Date of Patent: Nov. 6, 2012

(54) BACILLUS THURINGIENSIS STRAIN FOR INHIBITING INSECT PESTS

(75) Inventors: Ching-Chou Tzeng, Taichung County (TW); Sheueh Kuo, Taichung County (TW); Suey-Sheng Kao, Taichung County (TW)

(73) Assignee: Taiwan Agricultural Chemicals and Toxic Substances Research Institute, Council of Agriculture, Wufeng Shiang, Taichung County (TW)

( * ) Notice: Subject to any disclaimer, the term of this patent is extended or adjusted under 35 U.S.C. 154(b) by 259 days.

(21) Appl. No.: 12/564,478

(22) Filed: Sep. 22, 2009

(65) Prior Publication Data

US 2011/0027246 A1 Feb. 3, 2011

(30) Foreign Application Priority Data

Jul. 30, 2009 (TW) ................................ 98125751 A

(51) Int. Cl.
*C12N 1/20* (2006.01)
*A11N 63/00* (2006.01)
(52) U.S. Cl. ................ 435/252.5; 435/832; 424/93.461; 504/117

(58) Field of Classification Search ........................ None
See application file for complete search history.

(56) References Cited

U.S. PATENT DOCUMENTS 6,825,006 B2 * 11/2004 Baum et al. .................. 435/69.1

OTHER PUBLICATIONS

Theunis et al. "*Bacillus thuringiensis* isolates from the Philippines: habitat distribution, δ-endotoxin diversity, and toxicity to rice stem borers (Lepidoptera: Pyralidae)". Bulletin of Entomological Research (1998), vol. 88, No. 3, pp. 335-342.*
Srinivasan et al. "Susceptibility of major lepidopterans to δ-endotoxins and a formulation of *Bacillus thuringiensis* (B.t.) on vegetable brassicas in Taiwan". Biocontrol Science and Technology, vol. 18, No. 9, 2008, pp. 935-939.*
Srinivasan R. "Susceptibility of legume pod borer (LPB), *Maruca vitrata* to d-endotoxins of *Bacillus thuringiensis* (Bt) in Taiwan". Journal of Invertebrate Pathology (2008) 97: 79-81.*

* cited by examiner

*Primary Examiner* — Vera Afremova
(74) *Attorney, Agent, or Firm* — Muncy, Geissler, Olds & Lowe, PLLC

(57) ABSTRACT

A novel bacterial strain of *Bacillus thuringiensis* for inhibiting insect pests is provided, wherein the *Bacillus thuringiensis* includes the gene fragments of cry1Ab, cry1Ac, cry1D, and cry1E.

8 Claims, 2 Drawing Sheets

SEQUENCE LISTING

```
<160> NUMBER OF SEQ ID NOS: 8

<210> SEQ ID NO 1
<211> LENGTH: 29
<212> TYPE: DNA
<213> ORGANISM: ARTIFICIAL SEQUENCE
<220> FEATURE:
<223> OTHER INFORMATION: cry1Ab SPECIFIC GENE(reverse primer)

<400> SEQUENCE: 1
ggtcgtggct atatccttcg tgtcacagc                                      29

<210> SEQ ID NO 2
<211> LENGTH: 23
<212> TYPE: DNA
<213> ORGANISM: ARTIFICIAL SEQUENCE
<220> FEATURE:
<223> OTHER INFORMATION: cry1Ab SPECIFIC GENE(forward primer)

<400> SEQUENCE: 2
gaattgcttt cataggctcc gtc                                            23

<210> SEQ ID NO 3
<211> LENGTH: 33
<212> TYPE: DNA
<213> ORGANISM: Artificial sequence
<220> FEATURE:
<223> OTHER INFORMATION: cry1 specific gene(reverse primer)

<400> SEQUENCE: 3
```

-continued

```
atcactgagt cgcttcgcat gtttgactttt ctc                33
```

```
<210> SEQ ID NO 4
<211> LENGTH: 22
<212> TYPE: DNA
<213> ORGANISM: artificial sequence
<220> FEATURE:
<223> OTHER INFORMATION: cry1Ac specific gene(forward primer)

<400> SEQUENCE: 4
tcacttccca tcgacatcta cc                              22

<210> SEQ ID NO 5
<211> LENGTH: 25
<212> TYPE: DNA
<213> ORGANISM: artificial sequence
<220> FEATURE:
<223> OTHER INFORMATION: cry1D specific gene(forward primer)

<400> SEQUENCE: 5
ggtacattta gatattcaca gccac                           25

<210> SEQ ID NO 6
<211> LENGTH: 22
<212> TYPE: DNA
<213> ORGANISM: artificial sequence
<220> FEATURE:
<223> OTHER INFORMATION: cry1E specific gene(forward primer)

<400> SEQUENCE: 6
cttagggata aatgtagtac ag                              22

<210> SEQ ID NO 7
<211> LENGTH: 18
<212> TYPE: DNA
<213> ORGANISM: artificial sequence
<220> FEATURE:
<223> OTHER INFORMATION: cry2A specific gene(reverse primer)

<400> SEQUENCE: 7
aattccccat tcatctgc                                   18

<210> SEQ ID NO 8
<211> LENGTH: 24
<212> TYPE: DNA
<213> ORGANISM: artificial sequence
<220> FEATURE:
<223> OTHER INFORMATION: cry2A specific gene(forward primer)

<400> SEQUENCE: 8
actatttgtg atgcgtataa tgta                            24
```

BACILLUS THURINGIENSIS STRAIN FOR INHIBITING INSECT PESTS

FIELD OF THE INVENTION

The present invention relates to a novel microorganism of *Bacillus thuringiensis*. In particular, the present invention relates to a microorganism of *Bacillus thuringiensis* having fragments of cry1Ab, cry1Ac, cry1D, and cry1E genes. The present *Bacillus thuringiensis* used in anti-insect.

BACKGROUND OF THE INVENTION

Along with the respect to life quality and the rise of environmental protection consciousness, at present, the trend that the biological insecticides are substituted for the traditional pesticides to prevent the ultimate accumulation in the food chain has become the mainstream, in which *Bacillus thuringiensis* is the most famous application in the biological insecticides, and is easily utilized and safe.

*Bacillus thuringiensis*, a Gram-positive rod bacterium, is an insectile pathogenic bacterium. *B. thuringiensis* will progress into the non-mitotic semi-stationary phase or differentiate to form the spore or the insecticidal crystal protein while lacking nutrient or staying in the worse environment. The insecticidal crystal protein produced from *B. thuringiensis* can inhibit the growth of some insect pests, but is not harmful to mammals and birds. Therefore, scientists have been isolated various insecticidal genes from *B. thuringiensis*, and developed as the recombinant genetic products.

The endotoxin gene of *B. thuringiensis* is located on the plasmid thereof, so as to proceed the generic engineering easily. In the early stage, the recombinant endotoxin genes almost are limited in the cloning of single gene fragment. Recently, the multiple endotoxin genes or the genes with large diversities, even the chimeric genes, are utilized so as to improve the insecticidal effect, enlarge the insecticidal area or modify the resistance of *B. thuringiensis* to the worse environment.

The parental relationships among various endotoxin proteins of *B. thuringiensis* are different because of the insecticidal crystal proteins produced from the divergent nucleotide sequences of plasmids thereof. The insecticidal targets also are different, which are classified as six groups (Hofte and Whiteley, 1989; Gill et al., 1992; Gleave et al., 1993; Lereclus et al., 1993; Shin et al., 1995; Kostichka et al., 1996). Among these literatures, Cry1 protein family has the insecticidal effect to Lepidoptera; Cry2 protein family shows the insecticidal effect to Lepidoptera and Diptera, or only has the insecticidal effect to Diptera; Cry3 protein family has the insecticidal effect to Coleoptera; and Cry4 protein family only has the insecticidal effect to Diptera. Cry5 protein family cannot form as crystal protein, wherein Lepidoptera and Coleoptera can be killed by some part of Cry5 proteins but cannot be killed by other part thereof. CytA protein does not have specific insecticidal scope; however, the cytolytic and hemolytic effects can be induced by CytA protein. The cry1 gene of *B. thuringiensis* encodes the longest amino acid sequence, and cytA gene thereof encodes the shortest one.

Taiwan Patent No. 385229 relates to novel biopesticidal compositions comprising an active insecticidal ingredient selected from insecticidal bacteria and viruses such as *B. thuringiensis* crystal protein or spores or mixtures thereof and baculoviruses such as nuclear polyhedrosis viruses, granulosis viruses and non-occluded viruses. Methods for producing the biopesticidal compositions and methods of controlling insects are also included within the scope of the invention.

The differences between the Taiwan patent No. 385229 and present patent lie on the way to anti insect. It is the endotoxin produced by the gene fragments are used to anti pest, rather than the crystal protein or spores or mixtures thereof and baculoviruses.

U.S. Pat. No. 6,500,617 provides methods of obtaining pest resistance genes that are improved over naturally occurring genes for use in conferring upon plants resistance to pests. The methods involve the use of DNA shuffling of pest resistance genes to produce libraries of recombinant pest resistance genes, which are then screened to identify those that exhibit the improved property or properties of interest. The present invention uses a naturally method to obtain the anti insect fragments, while the U.S. Pat. No. 6,500,617 uses an method with recombinant DNA.

The U.S. Pat. No. 6,177,615 disclosed a novel synthetically-modified *B. thuringiensis* nucleic acid segments encoding delta-endotoxins having insecticidal activity against lepidopteran insects. Also disclosed are synthetic crystal proteins encoded by these novel nucleic acid sequences. The differences between the U.S. Pat. No. 6,177,615 and the present patent lie on which the anti insect fragments of *B. thuringiensis* in present invention are naturally existent not by artificial synthesize.

The U.S. Pat. No. 5,994,266 relates to a method for controlling a pest comprising exposing the pest to the pesticidal compositions. The differences between the U.S. Pat. No. 5,994,266 and the present patent lie on which the anti insect fragments of *B. thuringiensis* in present invention are naturally existent not by artificial synthesize.

Therefore, scientists are still exploring the microorganism with multiple endotoxin genes isolated by generic engineering or isolated by natural selection.

It is therefore attempted by the applicant to deal with the above situation encountered in the prior art.

SUMMARY OF THE INVENTION

The first purpose of the present invention, an isolated microorganism of *Bacillus thuringiensis* for inhibiting an insect is provided. A *Bacillus thuringiensis* strain which includes fragments of cry1Ab, cry1Ac, cry1D, and cry1E genes was identified by PCR selection.

The second purpose of the present invention, an isolated microorganism of *Bacillus thuringiensis* for inhibiting an insect is provided which can be manufactured into a insect controlling composition. The present composition carries an acceptable carrier and further comprising an effective dosage of an endotoxin.

In accordance with the first aspect of the present invention, an isolated microorganism of *Bacillus thuringiensis* for inhibiting an insect is provided. The microorganism includes fragments of cry1Ab, cry1Ac, cry1D, and cry1E genes.

Preferably, the isolated microorganism further includes a fragment of a cry2A gene.

Preferably, the insect has an order of Lepidoptera and a family being one selected from a group consisting of Noctuidae, Pyralidae and Plutellidae.

Preferably, the family of Noctuidae includes a species being one selected from a group consisting of *Helicoverpa armigera* and *Trichoplusia ni*.; the family of Pyralidae includes a species being one of *Maruca vitrata*, *Ephestia cautella* and *Crocidalomia binotalis*; and the family of Plutellidae includes a species of *Plutella xylostella*.

In accordance with the second aspect of the present invention, a pesticidal composition including *Bacillus thuringien-*

*sis* is provided. *B. thuringiensis* has fragments of cry1Ab, cry1Ac, cry1D, and cry1E genes.

Preferably, the pesticidal composition further includes an effective dosage of an endotoxin, and the endotoxin further is a δ-endotoxin.

Preferably, the pesticidal composition further includes a pharmaceutically acceptable carrier.

Preferably, *B. thuringiensis* further includes a fragment of a cry2A gene.

In accordance with the third aspect of the present invention, an inhibition method for an insect is provided. The inhibition method includes a step of applying *Bacillus thuringiensis* comprising fragments of cry1Ab, cry1Ac, cry1D, and a cry1E genes on a specific target.

Preferably, *B. thuringiensis* has an effective dosage for inhibiting the insect.

Preferably, the specific target is one selected from a group consisting of a crop, a cultivated land and a combination thereof.

In accordance with the fourth aspect of the present invention, an isolated microorganism of *Bacillus thuringiensis* having a DSM Accession No. 22750 is provided.

Preferably, the isolated microorganism further has a function being one selected from a group consisting of inhibiting an insect, producing a metabolite for antagonizing the insect, and being a raw material of a composition for inhibiting the insect.

Preferably, the metabolite is an endotoxin.

The bacterial strain of *Bacillus thuringiensis* F201 was deposited in the Deutsche Sammlung von Mikroorganismen and Zellkulturen (DSMZ) GmbH, Inhoffenstr. 7B, D-3 8124 Braunschweig, Germany, on Jul. 10, 2009, under the rules of Budapest Treaty, and the deposit number was DSM 22750.

The above objectives and advantages of the present invention will become more readily apparent to those ordinarily skilled in the art after reviewing the following detailed descriptions and accompanying drawings.

DETAILED DESCRIPTION OF THE PREFERRED EMBODIMENT

Figure 1:
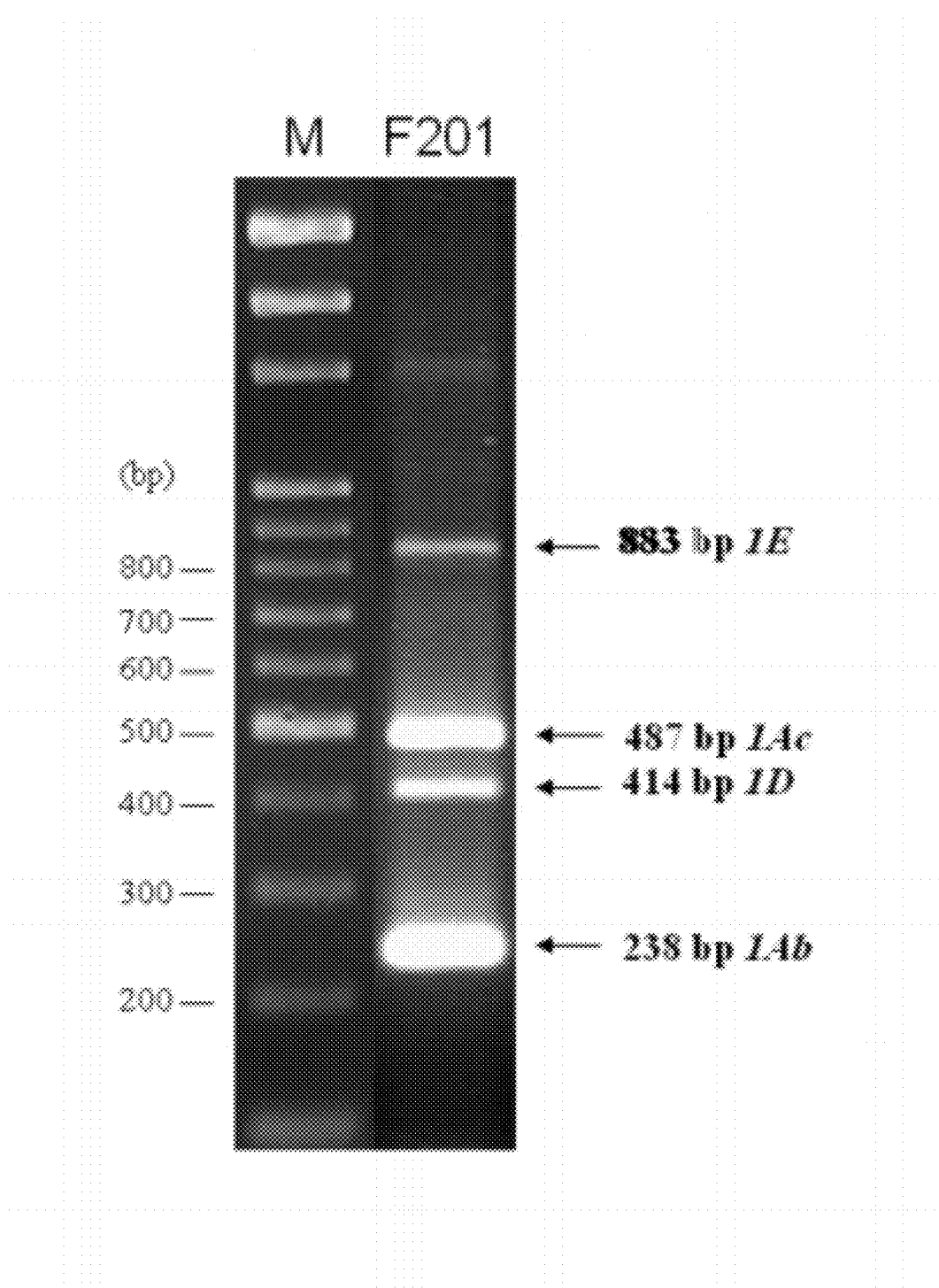
FIG. 1 is the electrophoresis pattern showing the endotoxin gene types of *B. thuringiensis* F201 strain of the present invention, and the endotoxin genes cry1Ab, cry1Ac, cry1D, and cry1E thereof are amplified by PCR.

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

A novel microorganism of *Bacillus thuringiensis* is provided in the present invention, and the bacterial strain can inhibit the growth of insect pests. The following detail descriptions illustrate the source, purification and isolation, identification and inhibition effect to the targeted pests of *B. thuringiensis*.

Sampling of Microorganism

Accordance with the method of Smith and Couche (1991), the plant with different families and species are collected from the Taipei Botanic Garden, a non-agriculture area. Choosing the branch 3 meters up from the ground, taking back with plastic bags and reserving in 4° C. refrigerator.

Isolation and Identification of Microorganism

Drying the plant in the shade first and taking 3 leaves from each branch. Triton X-100 (Amresco) diluted solution (50 ppm) 6 ml was used to wash the leaves and the washing buffer was collected. The washing buffer was centrifuged with 15,000×g, 6 min. The pellet was collected and resuspended with 0.5 ml distilled water (Smith and Couche, 1991). In accordance with the methods published in the literatures of Akiba and Katch (1986), Travers et al. (1987), Chak and Yang (1990) and Chilcott and Wigley (1993). The heat-treated suspended samples are sprayed on the nutrient agar (NA) plates. After continuous incubation at 28° C. for five days, the isolation of single colony is performed. The nutrient agar plates are observed under the phase contrast microscope with the oil immersion lens with a magnification of 1,500×, for isolating the bacterial strain containing crystal protein and spore. The isolated bacterial strains are nominated and reserved at 4° C. (Kao et al., 1996).

Incubation of Microorganism

Each of the nominated bacterial strains is suspended in distilled water, and is incubated on the nutrient agar plates by streaking method for three times, to isolate and identify the bacterial strain un-polluted. Each single colony is inoculated in 5 ml of Luria-Bertani (LB) broth (containing 0.1% of Bacto-tryptone, 0.5% of Bacto-yeast extract and 1% of NaCl, pH 7.0), and incubated overnight at 28° C. at 250 rpm. The incubated broth of 0.5 ml is sub-cultured at a ratio of 1:10 in the same condition for 3 hours.

Identification of Bacterial Strain

The sub-cultured bacterial strains are analyzed, and one of the bacterial strains is selected to nominated as *B. thuringiensis* F201, which is analyzed for the bacterial morphology and the follow-up experiments.

Polymerase Chain Reaction (PCR) of DNA and Cloning of Plasmid

The endotoxin gene types of *B. thuringiensis* F201 strain of the present invention are identified in accordance with the combinations of the endotoxin-specific primers published in Kalman et al. (1993).

(1) Amplification of cry1Ab Gene Fragment

The annealing reaction and amplification of PCR are performed by the cry1Ab specific sequence as the reverse primer (i.e. SEQ ID NO. 1) and the cry1Ab specific sequence as the forward primer (i.e. SEQ ID NO. 2), to identify the existence of the cry1Ab gene fragment.

(2) Amplification of cry1Ac Gene Fragment

The annealing reaction and amplification of PCR are performed by the cry1 specific sequence as the reverse primer (i.e. SEQ ID NO. 3) and the cry1Ac specific sequence as the forward primer (i.e. SEQ ID NO. 4), to identify the existence of the cry1Ac gene fragment.

(3) Amplification of cry1D Gene Fragment

The annealing reaction and amplification of PCR are performed by the cry1 specific sequence as the reverse primer (i.e. SEQ ID NO. 3) and the cry1D specific sequence as the forward primer (i.e. SEQ ID NO. 5), to identify the existence of the cry1D gene fragment.

(4) Amplification of cry1E Gene Fragment

The annealing reaction and amplification of PCR are performed by the cry1 specific sequence as the reverse primer (i.e. SEQ ID NO. 3) and the cry1E specific sequence as the forward primer (i.e. SEQ ID NO. 6), to identify the existence of the cry1E gene fragment.

(5) Amplification of cry2A Gene Fragment

The annealing reaction and amplification of PCR are performed by the cry II A2 specific sequence as the reverse primer (i.e. SEQ ID NO. 7) and the cry II A1 specific sequence as the forward primer (i.e. SEQ ID NO. 8), to identify the existence of the cry2A gene fragment.

Combinations of Endotoxin Genes in *B. thuringiensi* F201 Strain

Please refer to FIG. 1, which is the electrophoresis pattern showing the endotoxin gene types of *B. thuringiensis* F201 strain of the present invention, and the endotoxin genes thereof are amplified by PCR. According to Kalman et al. (1993), the lengths of the anticipated specific fragments of cry1Ab, cry1Ac, cry1D, and cry1E, gene fragments respectively are 238, 487, 414, and 883 bp. Therefore, *B. thuringiensis* F201 strain of the present invention includes multiple endotoxin gene fragments of cry1Ab, cry1Ac, cry1D, and cry1E in accordance with the fragment lengths shown in FIG. 1. In addition, the DNA ladder in FIG. 1 is abbreviated as "M", and the unit is base pair abbreviated as bp.

Figure 2:
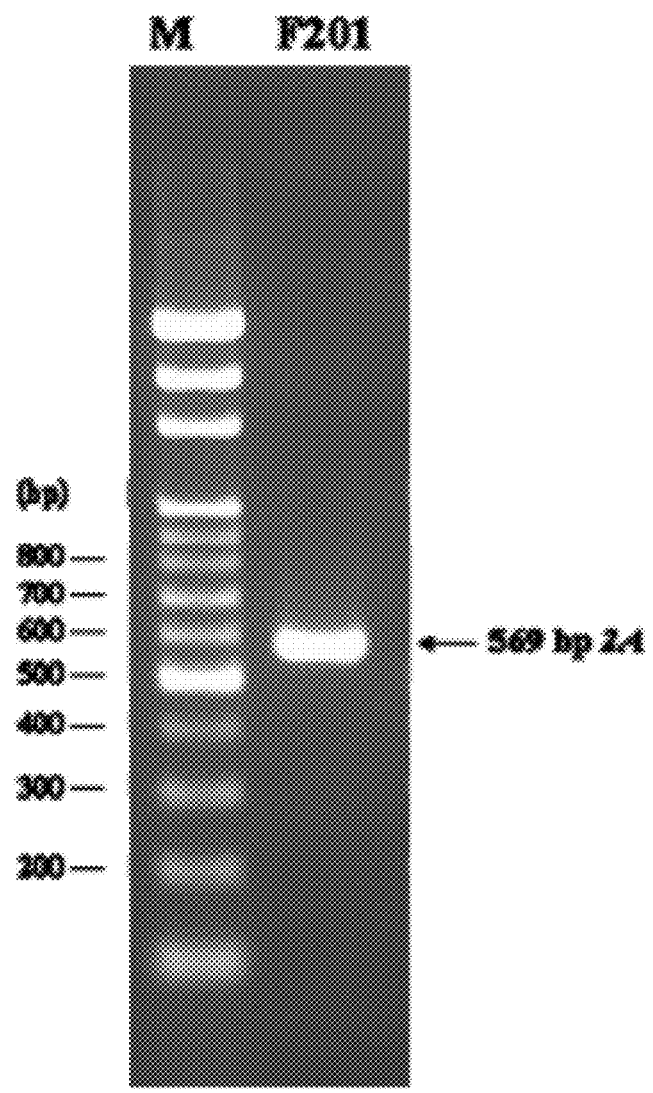
FIG. 2 is the electrophoresis pattern showing the endotoxin proteins of *B. thuringiensis* F201 strain of the present invention, and the endotoxin genes cry2A thereof is amplified by PCR.

Please refer to FIG. 2, which is the electrophoresis pattern showing the endotoxin proteins of *B. thuringiensis* F201 strain of the present invention, and the endotoxin genes thereof are amplified by PCR. According to Kalman et al. (1995), the lengths of the anticipated specific fragments of cry2A, gene fragment is 569 bp. Therefore, *B. thuringiensis* F201 strain of the present invention includes endotoxin gene fragment of cry2A in accordance with the fragment lengths shown in FIG. 2. In addition, the DNA ladder in FIG. 2 is abbreviated as "M", and the unit is base pair abbreviated as bp.

Inhibition activity of *B. thuringiensis* F201 to targeted insect pests

A composition with the insecticidal ability is further provided in the present invention, wherein the composition includes a culture of the effective dosage of *B. thuringiensis* F201 and the acceptable carrier. Further, endotoxin is contained in the culture. *B. thuringiensis* F201 or its mutant of the present invention is enriched by adapting industrial standard incubation method and fermentation. The fermented culture is tested to confirm the inhibition effect to the targeted insect pests.

There are three families of insect in the embodiment, Noctuidae, Pyralidae and Plutellidae. These insects are the pests of vegetable, pulse family crop and cellulose crop. They affect the flowering of the crop and influence the tassel forming which made huge damage on every-year's harvest.

To counter these insect, there are tests which treat the insect F201 and compare to the result of insect treat with Valent BioScience Xentari. The mortality of larvae was recorded. Table 1 lists out all the families and the testing insect. Table 2 is the total form which lists all the activity of *B. thuringiensis* F201 fermented culture to every testing insect.

TABLE 1

| The family of testing insect | | |
|---|---|---|
| Noctuidae | Pyralidae | Plutellidae |
| Helicoverpa armigera Trichoplusia ni | Maruca vitrata Crocidalomia binotalis Ephestia cautella | Plutella xylostella |

TABLE 2

| Activity of *B. thuringiensis* F201 fermented culture to every testing insect | | | | | | |
|---|---|---|---|---|---|---|
| Sample and treatment | H. armigera | T. ni | M. vitrata | C. binotalis | E. cautella | P. xylostella |
| Larve age | L2 | L2 | L3 | L3 | L3 | L3 |
| Concentration (ppm) | 500 | 12.5 | 100 | 50 | 100 | 2.5 |
| Treat time (hr) | 120 | 72 | 72 | 120 | 336 | 48 |
| Mortality of larve treating F201 (%) | 80.0 | 100 | 100 | 100 | 62.5 | 96.7 |
| Mortality of treating Xentari (%) | 40.0 | 6.7 | 75.0 | 85.7 | 54.9 | 85.0 |

The Noctuidae family include *Harmigera armigera* and *Trichoplusia ni*.

TABLE 3

| The *Noctuidae* family insect treatment | | |
|---|---|---|
| Sample and treatment | H. armigera | T. ni |
| Larve age | L2 | L2 |
| Concentration (ppm) | 500 | 12.5 |
| Treat time (hr) | 120 | 72 |
| Mortality of larve treating F201 (%) | 80.0 | 100 |
| Mortality of treating Xentari (%) | 40.0 | 6.7 |

Embodiment 1: *Helicoverpa armigera*

After *B. thuringiensis* F201 is enriched, five liters of the fermented culture is serially-diluted. *H. armigera* larvae in the early second instars nymph are treated with different diluted concentrations of fermented culture continuously for 120 hours by using feed mixture method. Thirty larvae are tested in each group, feed is not renovated, and the observation is continued. The numbers of dead larvae before and after the treatment of *B. thuringiensis* F201 are recorded, and the mortality of *H. armigera* larvae is calculated.

Please refer to Table 4, which is the inhibition activity of *B. thuringiensis* F201 fermented culture to *H. armigera*. While treating concentration is 500 ppm, the mortality of larvae is twice as the larvae treating with Xentari. *B. thuringiensis* F201 actually has the lethal effect to *H. armigera* in accordance with the result in Table 4.

TABLE 4

Inhibition activity of B. thuringiensis F201
fermented culture to Helicoverpa armigera

| Sample | Treat with F201 | Treat with Xentari | Control |
|---|---|---|---|
| No. of tested larvae | 30 | 30 | 30 |
| Concentration (ppm) | 500 | 500 | 0 ($H_2O$) |
| Treat time (hr) | 120 | 120 | 120 |
| Mortality (%) | 80.0 | 40.0 | 0 |

Embodiment 2: *Trichoplusia ni*

The preparation of the diluted fermented *B. thuringiensis* F201 cultures is identical with Embodiment 1. *T. ni* larvae in the early second instars nymph are treated with different diluted concentrations of fermented culture continuously for 72 hours by using feed mixture method. Fifty larvae are tested in each group, feed is not renovated, and the observation is continued. The numbers of dead larvae before and after the treatment of *B. thuringiensis* F201 are recorded, and the mortality of *T. ni* larvae is calculated.

Please refer to Table 5, which is the inhibition activity of *B. thuringiensis* F201 fermented culture to *T. ni*. Treating with only 12.5 ppm F201, the mortality of larvae achieved 100%, while the mortality of larvae treating with Xentari is only 6.7%. *B. thuringiensis* F201 actually has the lethal effect to *T. ni* in accordance with the result in Table 5.

TABLE 5

Inhibition activities of the B. thuringiensis
F201 fermented culture to Trichoplusia ni

| Sample | Treat with F201 | Treat with Xentari | Control |
|---|---|---|---|
| No. of tested larvae | 50 | 50 | 50 |
| Concentration (ppm) | 12.5 | 12.5 | 0 ($H_2O$) |
| Treat time (hr) | 72 | 72 | 72 |
| Mortality (%) | 100 | 6.7 | 0 |

The Pyralidae family include *Maruca vitrata*, *Crocidalomia binotalis* and *Ephestia cautella*.

TABLE 6

The Pyralidae family insect treatment

| Sample and treatment | M. vitrata | C. binotalis | E. cautella |
|---|---|---|---|
| Larve age | L3 | L3 | L3 |
| Concentration (ppm) | 100 | 50 | 100 |
| Treat time (hr) | 72 | 120 | 336 |
| Mortality of larve treating F201(%) | 100 | 100 | 62.5 |
| Mortality of treating Xentari (%) | 75.0 | 85.7 | 54.9 |

Embodiment 3: *Maruca vitrata*

The preparation of the diluted fermented *B. thuringiensis* F201 cultures is identical with Embodiment 1. *M. vitrata* larvae in the early third instars nymph are treated with different diluted concentrations of fermented culture continuously for 72 hours by using feed mixture method. Twenty four larvae are tested in each group, feed is not renovated, and the observation is continued. The numbers of dead larvae before and after the treatment of *B. thuringiensis* F201 are recorded, and the mortality of *M. vitrata* larvae is calculated.

Please refer to Table 7, which is the inhibition activity of *B. thuringiensis* F201 fermented culture to *M. vitrata*. While treating concentration is 100 ppm, the mortality of larvae is higher than the larvae treating with Xentari. *B. thuringiensis* F201 actually has the lethal effect to *M. vitrata* in accordance with the result in Table 7.

TABLE 7

Inhibition activities of the B. thuringiensis
F201 fermented culture to Maruca vitrata

| Sample | Treat with F201 | Treat with Xentari | Control |
|---|---|---|---|
| No. of tested larvae | 24 | 24 | 24 |
| Concentration (ppm) | 100 | 100 | 0 ($H_2O$) |
| Treat time (hr) | 72 | 72 | 72 |
| Mortality (%) | 100 | 75.0 | 0 |

Embodiment 4: *Crocidalomia binotalis*

The preparation of the diluted fermented *B. thuringiensis* F201 cultures is identical with Embodiment 1. *C. binotalis* larvae in the early third instars nymph are treated with different diluted concentrations of fermented culture continuously for 120 hours by using feed mixture method. Thirty larvae are tested in each group, feed is not renovated, and the observation is continued. The numbers of dead larvae before and after the treatment of *B. thuringiensis* F201 are recorded, and the mortality of *C. binotali* larvae is calculated.

Please refer to Table 8, which is the inhibition activity of *B. thuringiensis* F201 fermented culture to *C. binotalis*. While treating concentration is 50 ppm, the mortality of larvae is higher than the larvae treating with Xentari. *B. thuringiensis* F201 actually has the lethal effect to *C. binotalis* in accordance with the result in Table 8.

TABLE 8

Inhibition activities of the B. thuringiensis F201
fermented culture to Crocidalomia binotalis

| Sample | Treat with F201 | Treat with Xentari | Control |
|---|---|---|---|
| No. of tested larvae | 30 | 28 | 30 |
| Concentration (ppm) | 50 | 50 | 0 ($H_2O$) |
| Treat time (hr) | 120 | 120 | 120 |
| Mortality (%) | 100 | 85.7 | 0 |

Embodiment 5: *Ephestia cautella*

The preparation of the diluted fermented *B. thuringiensis* F201 cultures is identical with Embodiment 1. *E. cautella* larvae in the early third instars nymph are treated with different diluted concentrations of fermented culture continuously for 336 hours by using feed mixture method. Thirty larvae are tested in each group, feed is not renovated, and the observation is continued. The numbers of dead larvae before and after the treatment of *B. thuringiensis* F201 are recorded, and the mortality of *E. cautella* larvae is calculated.

Please refer to Table 9, which is the inhibition activity of *B. thuringiensis* F201 fermented culture to *E. cautella*. While treating concentration is 100 ppm, the mortality of larvae is higher than the larvae treating with Xentari. *B. thuringiensis* F201 actually has the lethal effect to *E. cautella* in accordance with the result in Table 9.

TABLE 9

Inhibition activities of the B. thuringiensis
F201 fermented culture to Ephestia cautella

| Sample | Treat with F201 | Treat with Xentari | Control |
|---|---|---|---|
| No. of tested larvae | 30 | 30 | 30 |
| Concentration (ppm) | 100 | 100 | 0 ($H_2O$) |

TABLE 9-continued

Inhibition activities of the *B. thuringiensis*
F201 fermented culture to *Ephestia cautella*

| Sample | Treat with F201 | Treat with Xentari | Control |
|---|---|---|---|
| Treat time (hr) | 336 | 336 | 336 |
| Mortality (%) | 62.5 | 54.9 | 0 |

The Plutellidae family include *Plutella xylostella*.

TABLE 10

The *Plutellidae* family insect treatment

| Sample and treatment | *Plutella xylostella* |
|---|---|
| Larve age | L3 |
| Concentration (ppm) | 2.5 |
| Treat time (hr) | 48 |
| Mortality of larve treating F201(%) | 96.7 |
| Mortality of treating Xentari (%) | 85.0 |

Embodiment 6: *Plutella xylostella*

The preparation of the diluted fermented *B. thuringiensis* F201 cultures is identical with Embodiment 1. *P. xylostella* larvae in the early third instars nymph are treated with different diluted concentrations of fermented culture continuously for 48 hours by using feed mixture method. Thirty larvae are tested in each group, feed is not renovated, and the observation is continued. The numbers of dead larvae before and after the treatment of *B. thuringiensis* F201 are recorded, and the mortality of *P. xylostella* larvae is calculated.

Please refer to Table 11, which is the inhibition activity of *B. thuringiensis* F201 fermented culture to *P. xylostella*. While treating concentration is 2.5 ppm, the mortality of larvae is higher than the larvae treating with Xentari. *B. thuringiensis* F201 actually has the lethal effect to *P. xylostella* in accordance with the result in Table 11.

TABLE 11

Inhibition activities of the *B. thuringiensis*
F201 fermented culture to *Plutella xylostella*

| Sample | Treat with F201 | Treat with Xentari | Control |
|---|---|---|---|
| No. of tested larvae | 30 | 30 | 30 |
| Concentration (ppm) | 2.5 | 2.5 | 0 ($H_2O$) |
| Treat time (hr) | 48 | 48 | 48 |
| Mortality (%) | 96.7 | 85.0 | 0 |

In conclusion, the isolated *Bacillus thuringiensis* F201 of the present invention actually is a novel bacterial strain of *Bacillus thuringiensis*, which contains endotoxin gene fragments of cry1Ab, cry1Ac, cry1D and cry1E. Further, the bacterial strain of *B. thuringiensis* has inhibition ability to the insect pests, such as *Helicoverpa armigera, Trichoplusia ni, Maruca vitrata, Crocidalomia binotalis, Ephestia cautella* and *Plutella xylostella*, etc.

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. An isolated microorganism of *Bacillus thuringiensis*, wherein the isolated microorganism comprises fragments of cry1Ab, cry1Ac, cry1D, and cry1E genes, wherein the isolated microorganism of *Bacillus thuringiensis* is deposited as a DSM Accession No. 22750, wherein the isolated microorganism is capable of inhibiting an insect belonging to an order of Lepidoptera and belonging to a family being one selected from a group consisting of Noctuidae, Pyralidae and Plutellidae.

2. The isolated microorganism according to claim 1 further comprising a fragment of cry2A gene.

3. The isolated microorganism according to claim 1, wherein the insect belonging to the family of Noctuidae comprises a species being one selected from a group consisting of *Helicoverpa armigera* and *Trichoplusia ni*.

4. The isolated microorganism according to claim 1, wherein the insect belonging to the family of Pyralidae comprises a species being one of *Maruca vitrata, Crodidalomia binotalis, Ephestia cautella*.

5. The isolated microorganism according to claim 1, wherein the insect belonging to the family of Plutellidae comprises a species of *Plutella xylostella*.

6. A pesticidal composition comprising an isolated microorganism of *Bacillus thuringiensis* having fragments of cry1Ab, cry1Ac, cry1D, and cry1E genes, wherein the isolated microorganism of *Bacillus thuringiensis* is deposited as a DSM Accession No. 22750, wherein the isolated microorganism is capable of inhibiting an insect belonging to an order of Lepidoptera and belonging to a family being one selected from a group consisting of Noctuidae, Pyralidae-and Plutellidae.

7. The pesticidal composition according to claim 6 further comprising a pharmaceutically acceptable carrier.

8. The pesticidal composition according to claim 6, wherein *Bacillus thuringiensis* further comprises a fragment of a cry2A gene.

* * * * *